(12) United States Patent
Lakis (10) Patent No.: US 11,147,959 B1
(45) Date of Patent: Oct. 19, 2021

(54) SYRINGE APPARATUS FOR DISINFECTION OF CENTRAL LINE PORT NEEDLELESS CONNECTOR AND METHOD OF DISINFECTING A CENTRAL LINE PORT NEEDLELESS CONNECTOR

(71) Applicant: Jason Lakis, La Mesa, CA (US)

(72) Inventor: Jason Lakis, La Mesa, CA (US)

( * ) Notice: Subject to any disclaimer, the term of this patent is extended or adjusted under 35 U.S.C. 154(b) by 0 days.

(21) Appl. No.: 17/218,298

(22) Filed: Mar. 31, 2021

(51) Int. Cl.
*A61M 39/16* (2006.01)
*A61M 39/20* (2006.01)
*A61M 5/315* (2006.01)
*A61M 5/31* (2006.01)

(52) U.S. Cl.
CPC ............ *A61M 39/16* (2013.01); *A61M 5/315* (2013.01); *A61M 5/3129* (2013.01); *A61M 39/20* (2013.01)

(58) Field of Classification Search
CPC .... A61M 39/16; A61M 5/315; A61M 5/3129; A61M 39/20
See application file for complete search history.

(56) References Cited

U.S. PATENT DOCUMENTS

| | | |
|---|---|---|
| 9,700,710 B2 | 6/2017 | Anderson et al. |
| 9,707,350 B2 | 7/2017 | Anderson et al. |
| 10,369,272 B2 | 8/2019 | Perrenoud et al. |
| 2004/0092890 A1 | 5/2004 | Ash |
| 2004/0156908 A1 | 8/2004 | Polaschegg |
| 2010/0145251 A1 | 6/2010 | Polaschegg |
| 2010/0211020 A1* | 8/2010 | Layton, Jr. ............ A61M 39/16 604/247 |
| 2013/0085474 A1* | 4/2013 | Charles ............... A61M 39/162 604/513 |
| 2013/0172260 A1 | 7/2013 | Polaschegg |
| 2017/0182305 A1 | 6/2017 | Kermode et al. |
| 2017/0361023 A1 | 12/2017 | Anderson et al. |
| 2018/0056034 A1 | 3/2018 | Cynamon |
| 2018/0085568 A1* | 3/2018 | Drmanovic ......... A61M 5/3134 |
| 2018/0326177 A1 | 11/2018 | Williams |
| 2019/0314570 A1 | 10/2019 | Perrenoud et al. |
| 2019/0376822 A1 | 12/2019 | Bochenko |
| 2020/0072648 A1 | 3/2020 | DeKalb et al. |
| 2020/0121858 A1 | 4/2020 | Anderson et al. |

FOREIGN PATENT DOCUMENTS

| | | |
|---|---|---|
| CN | 101405042 A | 4/2009 |
| CN | 203507240 U | 4/2014 |
| CN | 205322930 U | 6/2016 |
| CN | 206304185 U | 7/2017 |
| CN | 207640731 U | 7/2018 |
| CN | 110706799 A | 1/2020 |
| CN | 210873743 U | 6/2020 |
| CN | 210873745 U | 6/2020 |

* cited by examiner

*Primary Examiner* — Lauren P Farrar
(74) *Attorney, Agent, or Firm* — Robinson IP Law, PLLC (57) ABSTRACT

A syringe apparatus for disinfection of central line port needleless connector and method of disinfecting a central line port needleless connector. The syringe apparatus includes a syringe tip including a first O-ring including a disinfectant located in a first section of a tip cavity between an inner tip portion of the syringe tip and an outer tip portion of the syringe tip. The syringe tip preferably further includes one or more Luer lock sections and one or more additional O-rings. The syringe apparatus preferably also includes a cap including an inner layer including a disinfectant.

15 Claims, 9 Drawing Sheets

FIG. 12

SYRINGE APPARATUS FOR DISINFECTION OF CENTRAL LINE PORT NEEDLELESS CONNECTOR AND METHOD OF DISINFECTING A CENTRAL LINE PORT NEEDLELESS CONNECTOR

FIELD

This disclosure relates to the field of disinfection of central line port needleless connectors. More particularly, this disclosure relates to a syringe apparatus for disinfecting central line port needleless connectors and a method of disinfecting central line port needless connectors.

BACKGROUND

Central intravenous lines (also known as central venous catheters) are a type of intravenous (IV) line that, instead of only being inserted peripherally with a small catheter, are inserted into a patient's arm or neck and have a much longer catheter length, often leading all the way up to the top of a patient's heart. Central IV lines are used regularly in the hospital setting to help manage sick patients. Central IV lines are preferred to peripheral IV lines because central lines are a safer route through which to receive medication, antibiotics, fluids, blood, and nutrition. Central IV lines are a much more versatile and a better long-term option than a simple peripheral IV line.

Luer locks are often used in association with central lines. Luer locks are fittings that are securely joined by means of a tabbed hub to a female fitting (needless connector) which screws into threads in a sleeve on a male fitting (often a Normal Saline flush tip). Needleless connectors (also referred to as access ports) are the access medium for central lines. Usually there are two or three port attachments per central line with Luer locks at the tips. When a Normal Saline syringe is screwed into a Luer lock of a port, a patient's bloodstream can be accessed. Connection of both ends of the Luer lock open the "highway" to the bloodstream. Normal Saline (NS) flushes often use 0.9% sodium chloride solution in a prefilled syringe that connects directly to a needleless connector via a Luer lock system. NS flushes are the primary source of initial access to a patient's bloodstream.

When a healthcare professional accesses a needleless connector on a central line, there are usually one or more cleaning protocols in place. Such protocols typically include cleaning the outside and the surrounding of the needleless connector with an alcohol pad for a minimum period of time (often fifteen seconds). A next step is to twist a normal saline syringe (male end) into a needleless port (female end) locking into the luer locks. Next, the Normal Saline solution is injected into the central line. Key factors in cleaning the needleless connectors are (1) providing enough intense friction while twisting and engulfing the top and sides of the needleless connector with an alcohol pad and (2) dry time or allowing complete dryness of the needleless connector before use. Doing these steps often leads to a safe and direct access to a patient's bloodstream.

Central lines are incredibly useful for nurses who access them multiple times every shift to administer medications, nutrition, draw blood and a multitude of other interventions. Central lines are fast, easy, and extremely reliable. The biggest problem with central lines is often with the needleless connectors. When not in use, the needleless connectors are usually left dangling on patient's skin, inadvertently touched by hospital employees, dirty bed sheets, or other unclean surfaces. This creates biofilm growth over a needleless connector and, if not cleaned properly before a NS flush connection, can push millions of bacteria cells directly into a patient's bloodstream. This can result in a patient getting a central line associated bloodstream infection (CLABSI). CLABSIs are serious infections due to bacteria entering into a patient's central line. Such infection infects a patient's blood, potentially leading to sepsis and eventual death through septic shock. It is believed that around 50% of all CLABSIs are from improper cleaning of the needleless connectors prior to NS flushes. CLABSIs are treatable with antibiotics but such infections increase hospital stay length and create a more aggressive course of treatment. CLABSIs cost hospitals billions of dollars annually.

Current practice to minimize or otherwise prevent CLABSIs in hospitals include slogans like "Scrub the Hub" meaning clean the needleless connector for at least 15 seconds before connecting a NS syringe. This practice is intended to minimize/eliminate biofilm growth on a needleless connector prior to introducing a NS flush to an access port. This slogan and practice is well intentioned but with nurses being stressed and rushed from patient to patient, properly scrubbing the hub does not happen every single time. Some nurses will sometimes use an alcohol pad for a few seconds to clean prior to port connection. Rarely will a nurse "scrub the hub" for the full 15 seconds or whatever is stipulated in their hospital's policy and procedures. This leads to a high number of CLABSIs which has very undesirable ramifications for patient prognosis and is extremely expensive to both the patient and the hospital. Needleless connector disinfection is frequently overlooked because of the immense workload of hospital practitioners paired with the high frequency in which needleless connector are accessed. Needless connector disinfection is variable at best and typically consists of a gentle wipe of an alcohol pad on the needleless connector before a flush is connected. CLABSIs then occur at a high rate.

One solution to help with this problem are Curos™ brand disinfecting caps for needleless connectors available from 3M based in Maplewood, Minn. These caps include disinfectant inside and can be attached to needleless connectors to clean them in a short period of time (i.e., a minute or so). Such caps can be kept on needleless connectors for up to seven days and keep needleless connectors clean. However, Curos caps are devices separate from needleless connectors and NS syringes. Curos caps still do not eliminate the variability of use.

What is needed, therefore, is a solution that does not require a separate cap or "scrub the hub" steps when engaging a NS syringe with a needleless connector of a central line. In this era of healthcare there is higher patient acuity and higher amounts of practitioner burnout and stress. In light of the COVID-19 pandemic, especially in the Intensive Care Units, practitioner time management and safe practice has never been as imperative. The variability of proper technique of disinfecting all intravenous needleless connectors needs to be taken out of practitioners hands and into a product that does it for them properly every single time.

SUMMARY

The above and other needs are met by a NS flush syringe apparatus that eliminates all the variables associated with improper or inadequate cleaning of a needleless port. The new NS flush described herein can be used with old protocols or stand alone as a new device to accomplish the same task.

In one aspect, a syringe apparatus is disclosed comprising a barrel; a plunger; and a syringe tip, the syringe tip further comprising an inner tip portion extending from a first end of the barrel to a distal end of the syringe tip; an outer tip portion concentrically positioned outside the inner tip portion, wherein the outer tip portion extends from a first end of the barrel to a distal end of the outer tip portion, and wherein the inner tip portion extends farther away from the barrel than the outer tip portion; a tip cavity formed between the inner tip portion and the outer tip portion, the tip cavity comprising a first section proximate to the distal end of the outer tip portion and a second section adjacent to the first section located closer to the barrel than the first section; a first O-ring inside the first section wherein the O-ring comprises a first disinfectant substance absorbed into the O-ring; and a first thread inside the second section extending inwardly and winding helically from an inner wall of the outer tip portion. Preferably, the outer tip portion flares outward along the distal end of the outer tip portion, preferably coinciding with the first section of the tip cavity. Preferably, saline solution is located inside the barrel.

The syringe tip preferably further comprises the tip cavity further comprising a third section adjacent to the second section and located closer to the barrel than the second section; and a second O-ring inside the third section wherein the second O-ring is dry. The syringe tip preferably further comprises the tip cavity further comprising a fourth section adjacent to the third section and located closer to the barrel than the third section; and a second thread inside the fourth section extending inwardly and winding helically from the inner wall of the outer tip portion.

In certain preferred embodiments, the syringe apparatus preferably further comprises a cap attached to the outer tip portion, the cap further comprising an outer shell; and an inner layer comprising a second disinfectant substance absorbed into the inner layer. The syringe preferably further comprises a seal ribbon wrapped around the interface between the cap and the outer tip portion, providing an air-tight seal that prevents drying of the first disinfectant substance in the cap and the second disinfectant substance in the first O-ring. In some embodiments, the first disinfectant substance comprises the second disinfectant substance. In some embodiments, the outer tip portion further comprises an outer ridge along the distal end of the outer tip portion, wherein the cap further comprises a bulge along a base of the cap, and wherein the seal ribbon is wrapped around the outer ridge and the bulge, sealing the cap to the outer tip portion.

In some embodiments, the syringe tip further comprises the tip cavity further comprising a third section adjacent to the second section and located closer to the barrel than the second section; and a second thread inside the third section extending inwardly and winding helically from the inner wall of the outer tip portion.

In another aspect, a method for disinfecting a needleless connector is disclosed, the method comprising inserting an inner tip portion of a syringe tip of a syringe apparatus into a receiving cavity of a needleless connector until a first end of the needleless connector reaches an outer tip portion of the syringe tip and compresses a first O-ring inside a tip cavity of the syringe tip defined between the inner tip portion and the outer tip portion to release disinfectant stored in the first O-ring onto the needleless connector; and twisting the syringe apparatus relative to the needleless connector to engage a first thread in the syringe tip with one or more connector ridges in the needleless connector. The method preferably further comprises pushing the syringe tip further into the receiving cavity to cause the one or more connector ridges to press against a second O-ring in the tip cavity of the syringe tip wherein the second O-ring is initially dry. The method preferably further comprises twisting the syringe tip relative to the needleless connector to engage a second thread in the syringe tip with one or more connector ridges in the needleless connector.

In another aspect, a method of injecting medicine into a patient through a central IV line is disclosed, the method comprising displacing liquid from a barrel of a syringe apparatus by pushing a plunger of the syringe inward; inserting a syringe tip of the syringe apparatus into a medicine vial; extracting medicine from the medicine vial using the syringe apparatus; disengaging the syringe apparatus from the medicine vial; inserting an inner tip portion of a syringe tip of a syringe apparatus into a receiving cavity of a needleless connector in fluid communication with a patient's bloodstream until a first end of the needleless connector reaches an outer tip portion of the syringe tip and compresses a first O-ring inside a tip cavity of the syringe tip defined between the inner tip portion and the outer tip portion to release disinfectant stored in the first O-ring onto the needleless connector; and injecting the extracted medicine from the syringe apparatus to the patient by injecting the extracted medicine to the needleless connector.

Preferably, the syringe tip used in the method comprises an inner tip portion extending from a first end of a barrel of the syringe apparatus to a distal end of the syringe tip; and an outer tip portion concentrically positioned outside the inner tip portion, wherein the outer tip portion extends from a first end of the barrel to a distal end of the outer tip portion a distance of length L, and wherein the inner tip portion extends away from the barrel than the outer tip portion a distance of more than the length L. The distal end of the syringe tip preferably comprises a multi-faceted blunt tip. Preferably, the inserting step d preferably further comprises twisting the syringe tip relative to the needleless connector to engage a first thread in the syringe tip with one or more connector ridges in the needleless connector. The inserting step d preferably further comprises pushing the syringe tip further into the receiving cavity to cause the one or more connector ridges to press against a second O-ring in the syringe tip. The inserting step d preferably further comprises twisting the syringe tip relative to the needleless connector to engage a second thread in the syringe tip with one or more connector ridges in the needleless connector.

The summary provided herein is intended to provide examples of particular disclosed embodiments and is not intended to cover all potential embodiments or combinations of embodiments. Therefore, this summary is not intended to limit the scope of the invention disclosure in any way, a function which is reserved for the appended claims.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

The figures are provided to illustrate concepts of the invention disclosure and are not intended to embody all potential embodiments of the invention. Therefore, the figures are not intended to limit the scope of the invention disclosure in any way, a function which is reserved for the appended claims.

DETAILED DESCRIPTION

Figure 1:
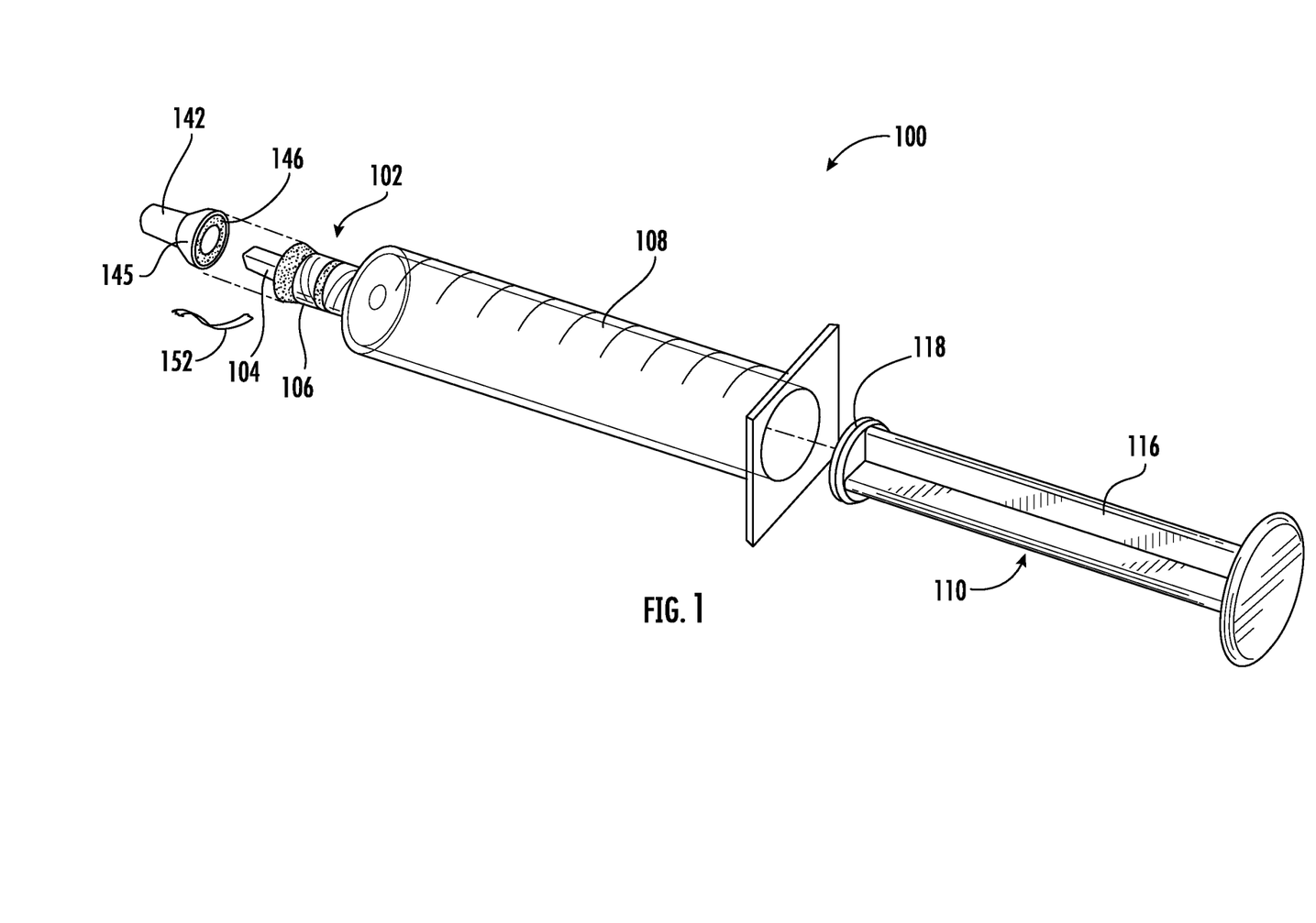
FIG. 1 shows a partially exploded view of a syringe apparatus as described herein.
Figure 2:
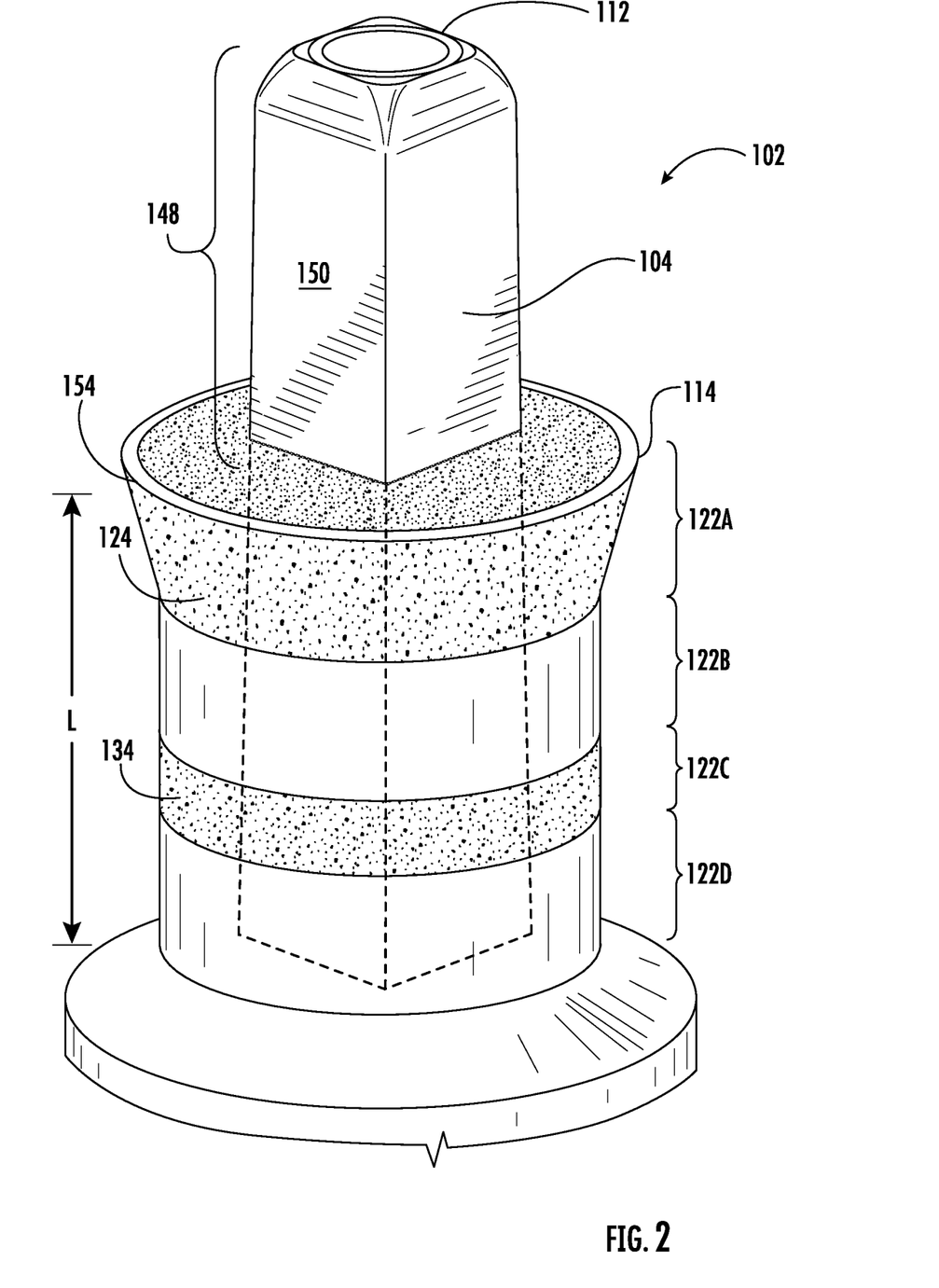
FIG. 2 shows a close-up view of a syringe tip of the syringe apparatus shown in FIG. 1.
Figure 8:
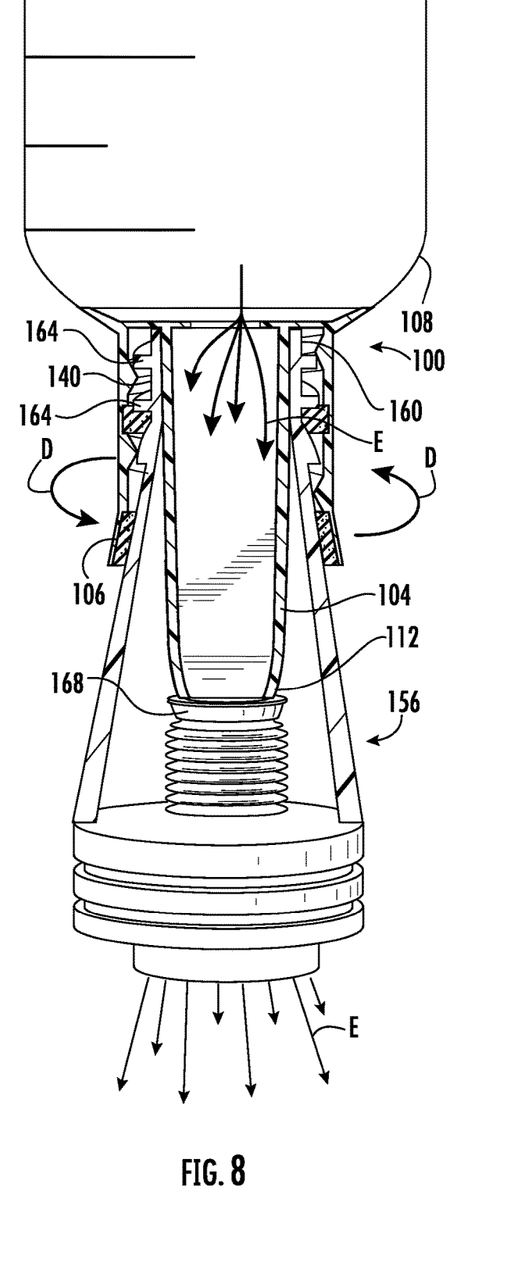
FIG. 8 shows a second "twist" step of engaging the syringe apparatus of FIGS. 1-6 (shown as a cross-sectional view) further into a needleless connector (shown as a cross-sectional view) and engaging Luer lock features between the syringe apparatus and the needleless connector.
Figure 9:
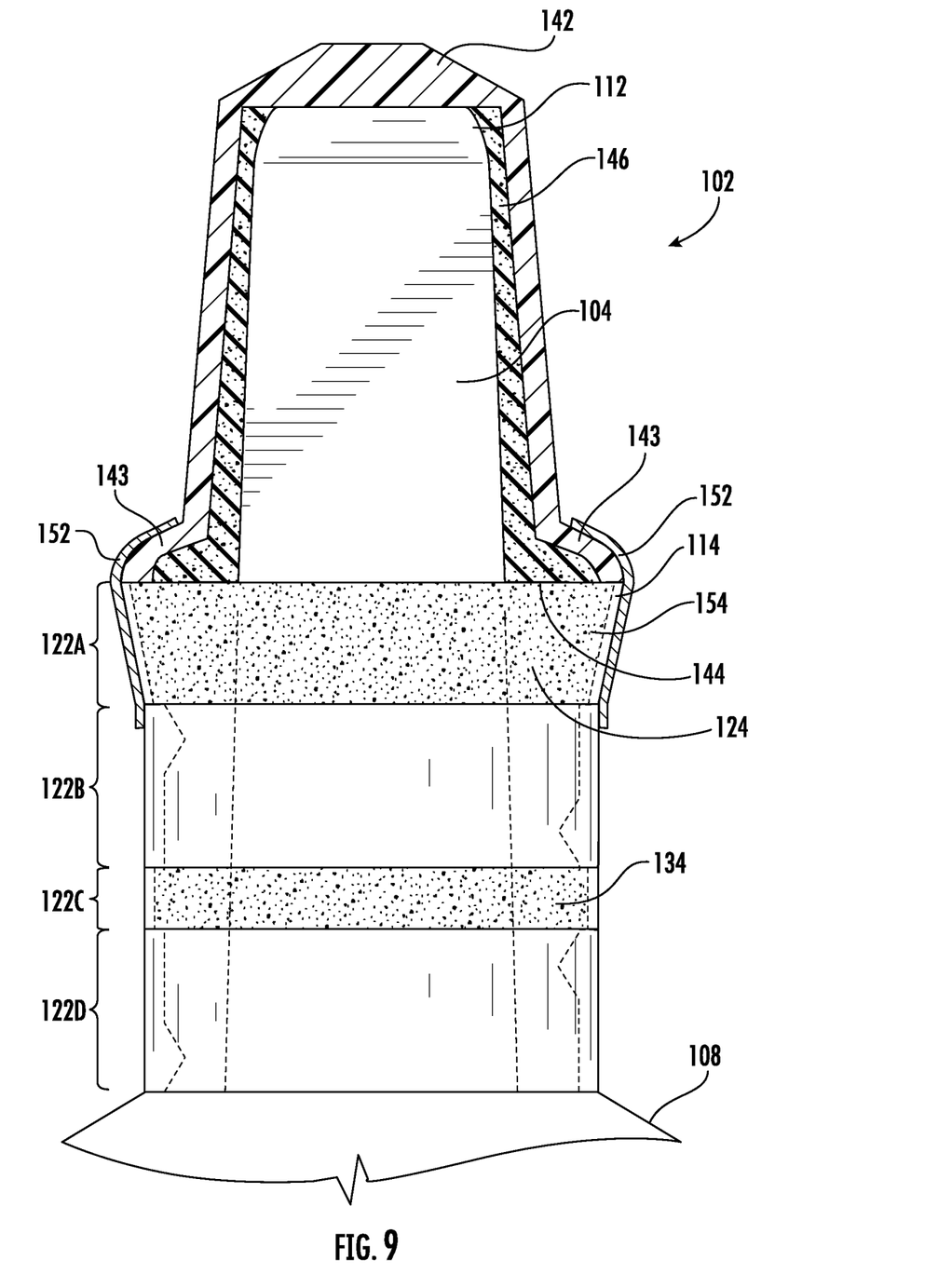
FIG. 9 shows a cross-sectional view of the syringe tip shown in FIG. 2 further showing a cap and seal ribbon on the syringe tip.
Figure 10:
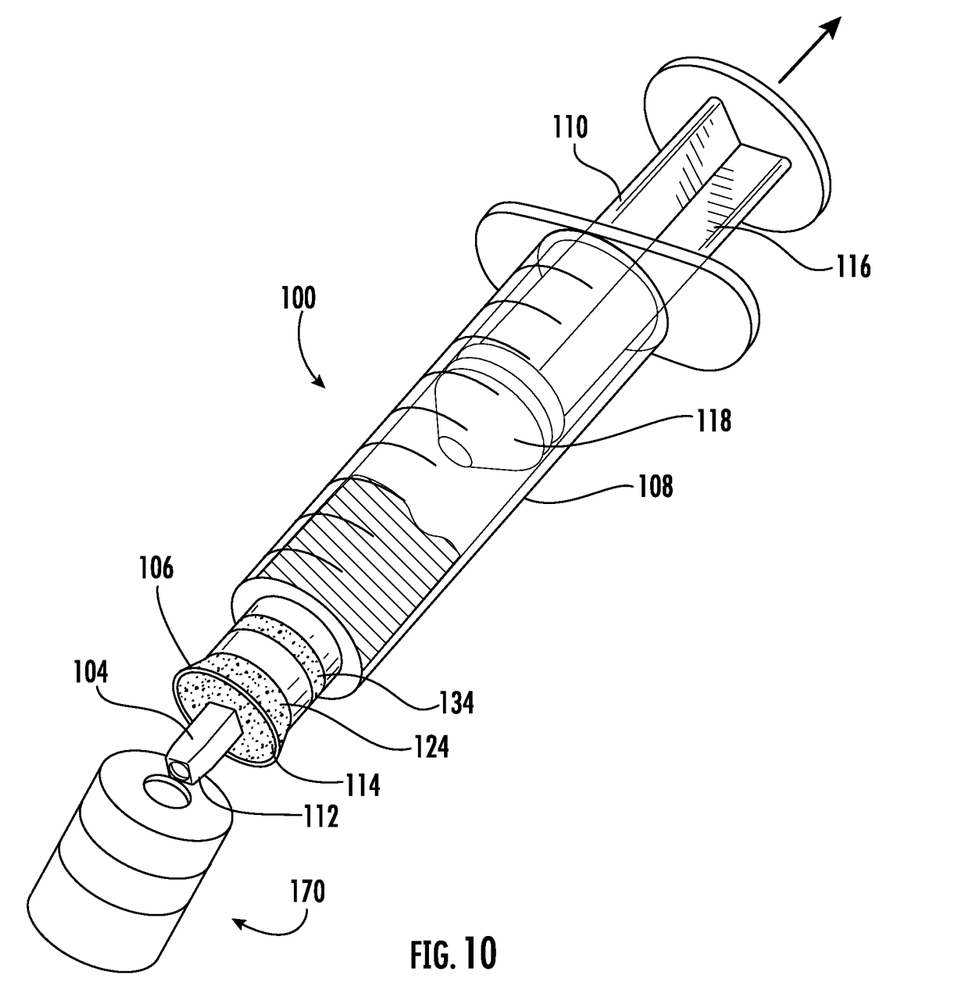
FIG. 10 shows the syringe apparatus shown in FIGS. 1-8 in proximity to a medicine vial wherein the blunt syringe tip shown in FIG. 2 is configured to penetrate such medicine vial to draw medicine out and then engage with a needleless connector to inject such medicine to a patient.
Figure 11:
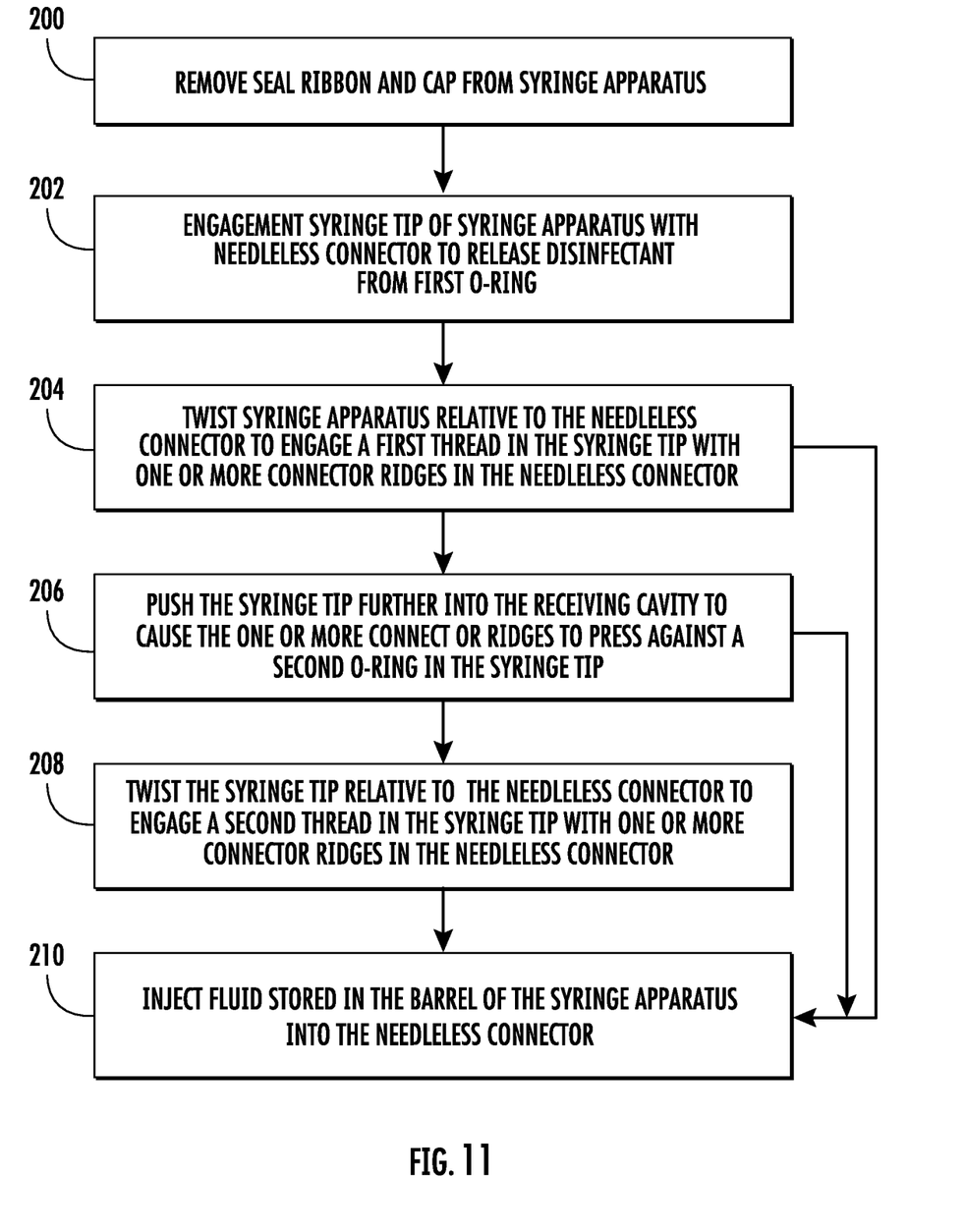
FIG. 11 shows a flow chart of method steps for using the syringe apparatus shown in FIGS. 1-9 for a Normal Saline flush including inserting the syringe tip of the syringe apparatus into a receiving cavity of a needleless connector and pushing the syringe tip further to make the first O-ring compress around the needleless connector, releasing disinfectant onto all surfaces of the needleless connector.

FIGS. 1-9 show various views of an embodiment of a syringe apparatus 100 for disinfection of central line port needleless connector of a central IV line. The syringe apparatus 100 includes a syringe tip 102 including a hollow inner tip portion 104 and an outer tip portion 106 which encircles the inner tip portion 104 like an outer wall. As shown, for example, in FIG. 3, the inner tip portion 104 is situated concentrically inside of the outer tip portion 106. As shown in FIG. 1 and FIG. 10, the syringe apparatus 100 also includes a barrel 108 for storing fluid wherein the barrel 108 is in fluid communication with the hollow inner tip portion 104. The syringe apparatus also includes a plunger 110 for driving stored fluid through the inner tip portion 104 and out a distal end 112 of the inner tip portion 104 when the syringe apparatus 100 is being used to insert fluid into a central IV line. The distal end 112 of the inner tip portion 104 preferably extends well beyond a distal end 114 of the outer tip portion 106 by about 3 millimeters (mm) to about 4 mm. Also, the distal end 112 of the inner tip portion 104 preferably has four sides and is preferably blunt and slightly rounded as shown in FIG. 2 and FIG. 10. The plunger includes a plunger rod 116 and a stopper 118, preferably made of rubber to prevent blood reflux. The syringe tip 102, syringe barrel 108, and syringe plunger 110 are preferably made of plastic like most conventional saline flush syringes. However, these structures can be made of other materials known to persons having ordinary skill in the art.

As shown in FIGS. 3-8, a tip cavity 120 is located between the inner tip portion 104 and the outer tip portion 106. Inside the tip cavity 120 are preferably four sections including a first section 122A, a second section 122B, a third section 122C, and a fourth section 122D. These sections are ordered starting from the distal end 114 of the outer tip portion 106. The first section 122A includes a sponge-like first O-ring 124 which preferably is saturated with a disinfecting substance (or "disinfectant"). The disinfectant is preferably isopropyl alcohol (preferably 70% pure isopropyl alcohol plus 30% purified water by volume), but other disinfectants, solutions, and mixtures known to a person having ordinary skill in the art can be used. The first O-ring 124 is preferably made of medical grade 100 pores per inch (PPI) open cell polyurethane foam and is preferably nestled into a first groove 126. The outer tip portion 106 further includes a first thread 130 (i.e., a ridge of uniform section in the form of a helix) extending inward from an inner wall surface 132 of the outer tip 106 in the second section 122B of the tip cavity 120. The first thread 130 preferably winds helically around the inner wall 132 of the outer tip portion 106 one and one-half (1.5) times. The third section 122C includes a second O-ring 134 preferably made of medical grade 100 PPI open cell polyurethane foam and preferably nestled into a second groove 136. The outer tip portion 106 further includes a second thread 140 extending inward from the inner wall surface 132 of the outer tip portion 106 in the fourth section 122D of the tip cavity 120. The second thread 140 preferably winds helically around the inner wall 132 of the outer tip portion 106 one and one-half (1.5) times.

The syringe apparatus 100 preferably comes pre-packaged with saline solution in the barrel 108. In a preferred pre-packaged configuration before use, the syringe apparatus 100 includes a cap 142. The cap preferably further includes a bulge 143 along a base 144 of the cap 142. The cap 142 preferably further includes an outer shell 145 and an inner layer 146 that is preferably saturated with a disinfectant. The inner layer 146 is preferably a sponge-like material made of medical grade 100 PPI open cell polyurethane foam, but other materials with the ability to absorb and hold disinfectant can be used. The disinfectant liquid is preferably isopropyl alcohol (preferably 70% pure isopropyl alcohol plus 30% purified water by volume). Other disinfecting liquids, solutions, and mixtures known to a person having ordinary skill in the art can be used. When in the preferred pre-packaged form, the cap 142 covers an external section 148 of the inner tip portion 104 such that disinfectant is in constant contact with an outer surface 150 of the external section 148 of the inner tip portion 104. The external section 148 of the inner tip portion 104 is referred to as "external" because it extends out beyond the outer tip portion 106, preferably by about 3 mm to about 4 mm. When in the preferred pre-packaged form, the syringe apparatus 100 further includes a seal ribbon 152 as shown in FIG. 9 for sealing the connection between the cap 142 and an outer ridge 154 along the distal end 114 of the outer tip portion. The seal ribbon 152 helps preserve the disinfectant in the inner layer 146 and the first O-ring 124 by slowing evaporation of the disinfectant. The seal ribbon 152 is preferably made of metal foil, preferably aluminum.

Figure 3:
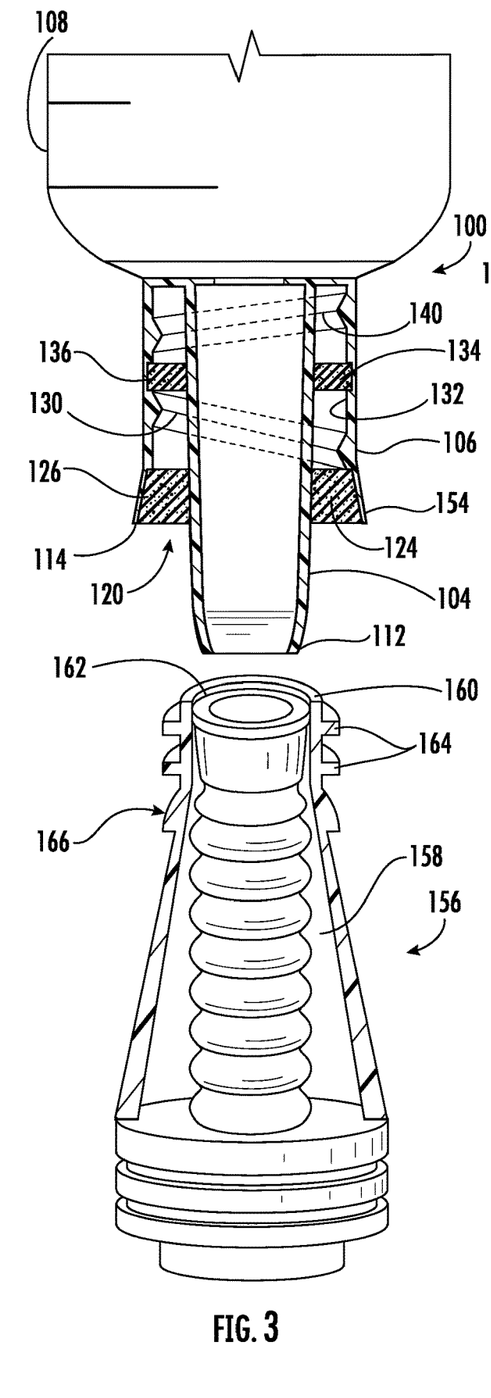
FIG. 3 shows a cross-sectional view of the syringe tip shown in FIG. 2 oriented to engage a needleless connector which is also shown as a cross-sectional view.

FIGS. 3-8 and FIG. 11 show some of the steps of engaging the syringe apparatus 100 with a needleless connector 156. A first step 200 is the removal of the seal ribbon 152 and the cap 142. The seal ribbon 152 is preferably torn off using a fingernail to start tearing the seal ribbon 152 off. An end of the seal ribbon 152 preferably sticks out like a tab and provides an easy way to start tearing the seal ribbon 152 off. Once the cap 142 is removed, the outer surface 150 of the inner tip portion 104 along the external section 148 of the inner tip portion is coated with disinfectant. FIG. 3 shows the syringe apparatus 100 with the cap 142 removed and oriented to engage with a needleless connector 156. The needleless connector 156 includes a receiving cavity 158 (female connector) to receive the inner tip portion 104 (male connector) of the syringe apparatus 100.

Figure 4:
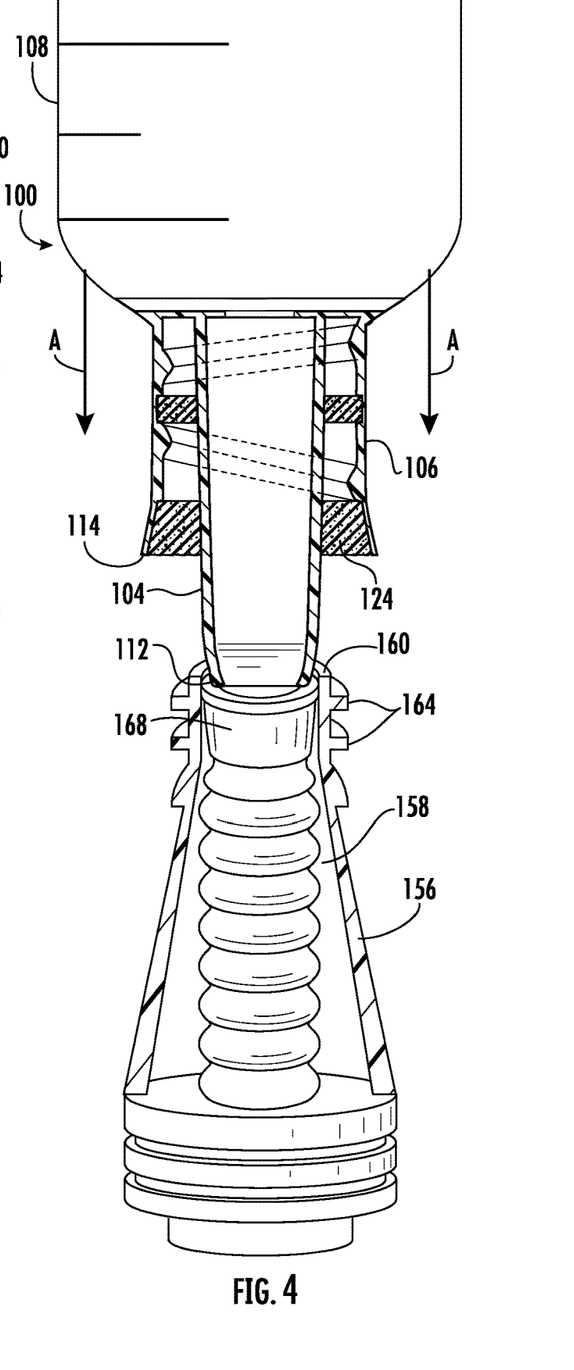
FIG. 4 shows initial contact of the syringe apparatus of FIGS. 1-3 (shown as a cross-sectional view) with a needleless connector (shown as a cross-sectional view)
Figure 5:
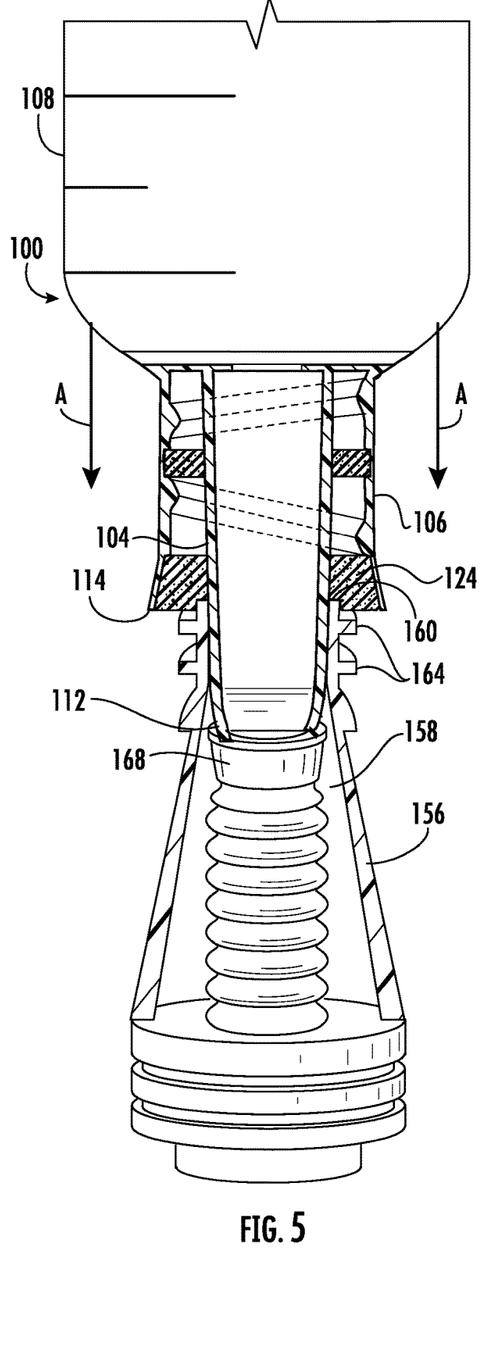
FIG. 5 shows a first "push" step of engaging the syringe apparatus with the needleless connector such that the needleless connector contacts and compresses a first O-ring containing disinfectant, thereby releasing the disinfectant onto the needless connector.

FIG. 4 shows the syringe apparatus 100 as it initially engages with the needleless connector 156 with the distal end 112 of the inner tip portion 104 contacting a first end 160 of the needleless connector 156 which includes a passage 162 providing an entrance to the receiving cavity 158. FIG. 5 shows the first end 160 of the needleless connector contacting the first O-ring 124 and compressing the first O-ring 124. This second step 202 of engaging the syringe tip 102 with the needleless connector 156 is the first of two "push" steps. Along the first end 160 of the needleless connector 156 are one or more connector ridges 164. During step 202 (this first "push" step as indicated by arrows A), the connector ridges 164 are pressed against and compress the first O-ring 124, thereby releasing disinfectant. At this point, disinfectant is located on the first end 160 of the needleless connector 156 wherein such disinfectant originated from the first O-ring 124 after it was compressed in step 202. During this step, the distal end 112 of the inner tip portion 104 comes into contact with a compressible sleeve 168 inside the needleless connector 156.

Figure 6:
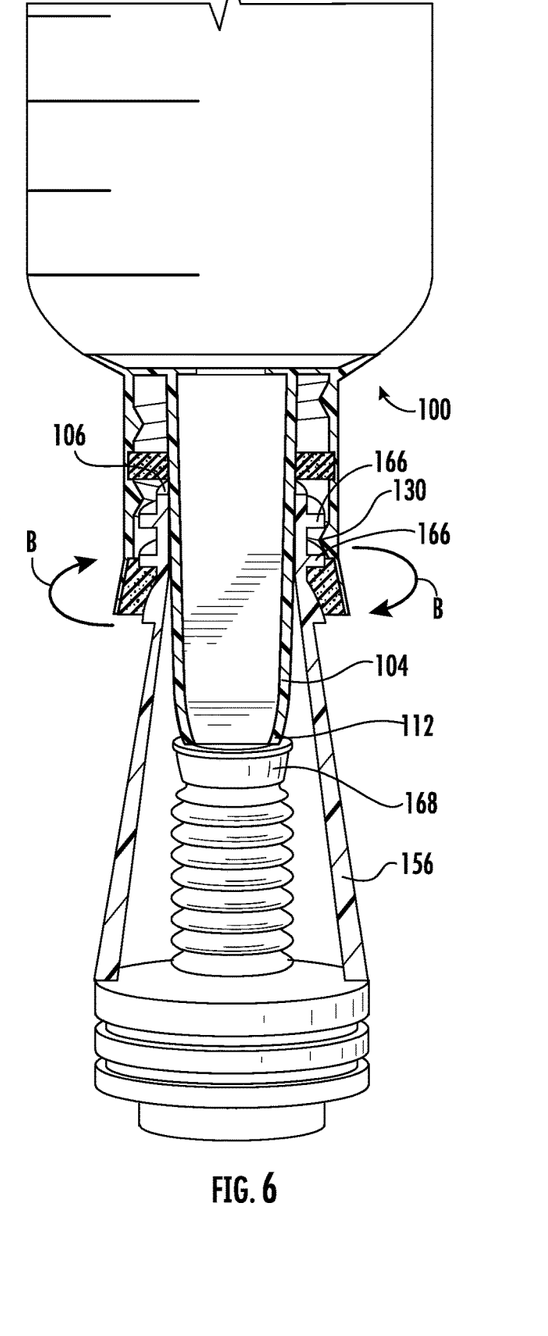
FIG. 6 shows a first "twist" step of engaging the syringe apparatus of FIGS. 1-4 (shown as a cross-sectional view) further into a needleless connector (shown as a cross-sectional view) and engaging Luer lock features between the syringe apparatus and the needleless connector.

FIG. 6 shows step 204 (a first "twist" step as indicated by arrows B) in which the connector ridges 164 begin to engage with the first thread 130 as the syringe apparatus 100 and needleless connector 156 are twisted relative to one another. The connector ridges 164, the first thread 130, and the second thread 140 are also commonly referred to as "Luer lock" or "Luer slip" features. The first end 160 of the needleless connector 156 passes by the first O-ring 124 into the second section 122B of the tip cavity 120, thereby displacing disinfectant along an outer surface 166 of the needleless connector 156 including the connector ridges 164. Disinfectant from the first O-ring 124 that was discharged during the first "push" step (step 202) is brought from the first section 122A into the second section 122B of the tip cavity 120 during step 204.

Figure 7:
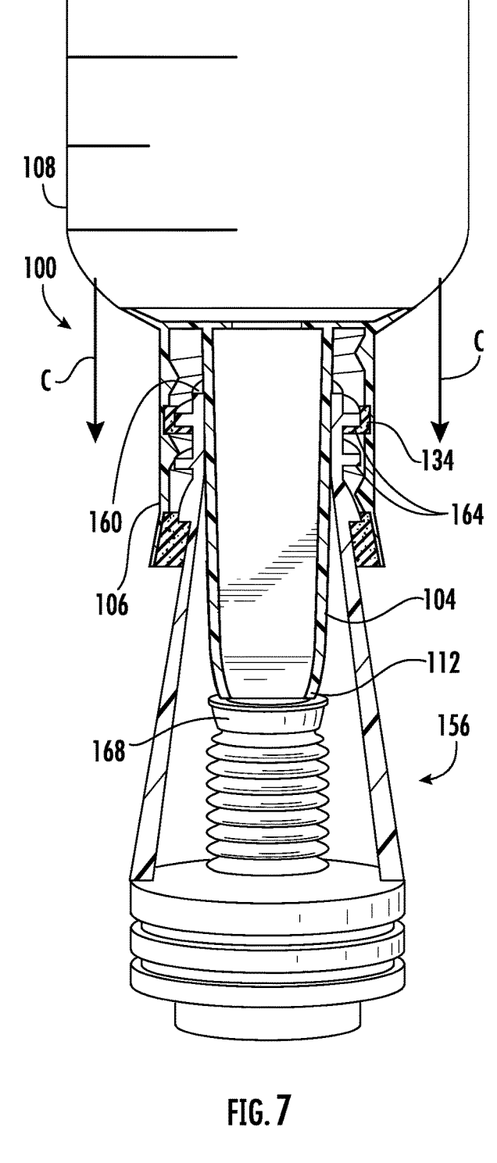
FIG. 7 shows a second "push" step of engaging the syringe apparatus of FIGS. 1-5 (shown as a cross-sectional view) with a needleless connector (shown as a cross-sectional view) such that the needleless connector presses against a second O-ring in the syringe tip.

FIG. 7 shows step 206 (a second "push" step as indicated by arrows C) in which the inner tip portion 104 of the syringe apparatus 100 is pushed and inserted farther into the receiving cavity 158 of the needleless connector 156. During step 206, the first end 160 of the needleless connector 156 extends into the third section 122C of the tip cavity 120. At this point, the first end 160 of the needleless connector 156 and the associated connector ridges 164 are pressed against the second O-ring 134 which preferably acts as a drying structure to dry disinfectant on the first end 160 of the needleless connector 156. One purpose for this is minimize the chances of disinfectant inadvertently being injected into a patient's bloodstream during a NS flush.

FIG. 8 shows step 208 (a second "twist" step as indicated by arrows D) in which the connector ridges 164 begin to engage with the second thread 140 as the syringe apparatus 100 and needleless connector 156 are twisted relative to one another. The first end 160 of the needleless connector 156 passes by the second O-ring 134 into the fourth section 122D of the tip cavity 120, securely locking the syringe apparatus 100 to the needleless connector 156. The now disinfected first thread 130, when twisted vigorously around the connector ridges 164, provides a tremendous friction induced anti septic environment for all surfaces of the needleless connector 156 (top, sides, and down length of the needleless connector 156). The syringe apparatus 100 utilizes mechanical motion in a closed system as a means of eliminating needleless connector 156 biofilm growth. The disinfected connection between the syringe apparatus 100 and the needleless connector 156 allows injection of fluid stored in the barrel 108 into the needleless connector 156 (step 210) which then passes through a central IV line in fluid communication with the needleless connector 156. This is shown as arrows E in FIG. 8.

The first section 122A of the syringe tip 102 preferably angles or flares outward as shown in FIGS. 2-10 such that it is slightly larger than the other sections (122B, 122C, and 122D). The first O-ring 124 is preferably larger than the second O-ring 134 because of the increased size of the first section 122A relative to the third section 122C. This flaring out of the first section 122A provides more space for needleless connectors as the syringe apparatus 100 moves down, across, and into a needleless connector. The syringe tip 102 is longer than contemporary syringe tips because of the additional features. Because some needleless connectors gradually increase in girth the farther down a syringe moves relative to such needleless connector, extra space is needed toward the distal end 114 of the outer tip portion 106. That is one reason for the preferred configuration in which the first section 122A is flared outward.

Simpler embodiments of the syringe apparatus 100 are contemplated including a syringe apparatus that does not include the third section 122C (and associated second O-ring 134) or the fourth section 122D (and the associated second thread 140). For such an embodiment, the syringe tip 102 would only include the first section 122A (and associated first O-ring 124) and the second section 122B (and associated first thread 130).

In a related simpler embodiment of the syringe apparatus 100, the syringe apparatus does not include the fourth section 122D (and the associated second thread 140). For such an embodiment, the syringe tip 102 would only include the first section 122A (and associated first O-ring 124), the second section 122B (and associated first thread 130), and the third section 122C (and associated second O-ring 134).

Figure 12:
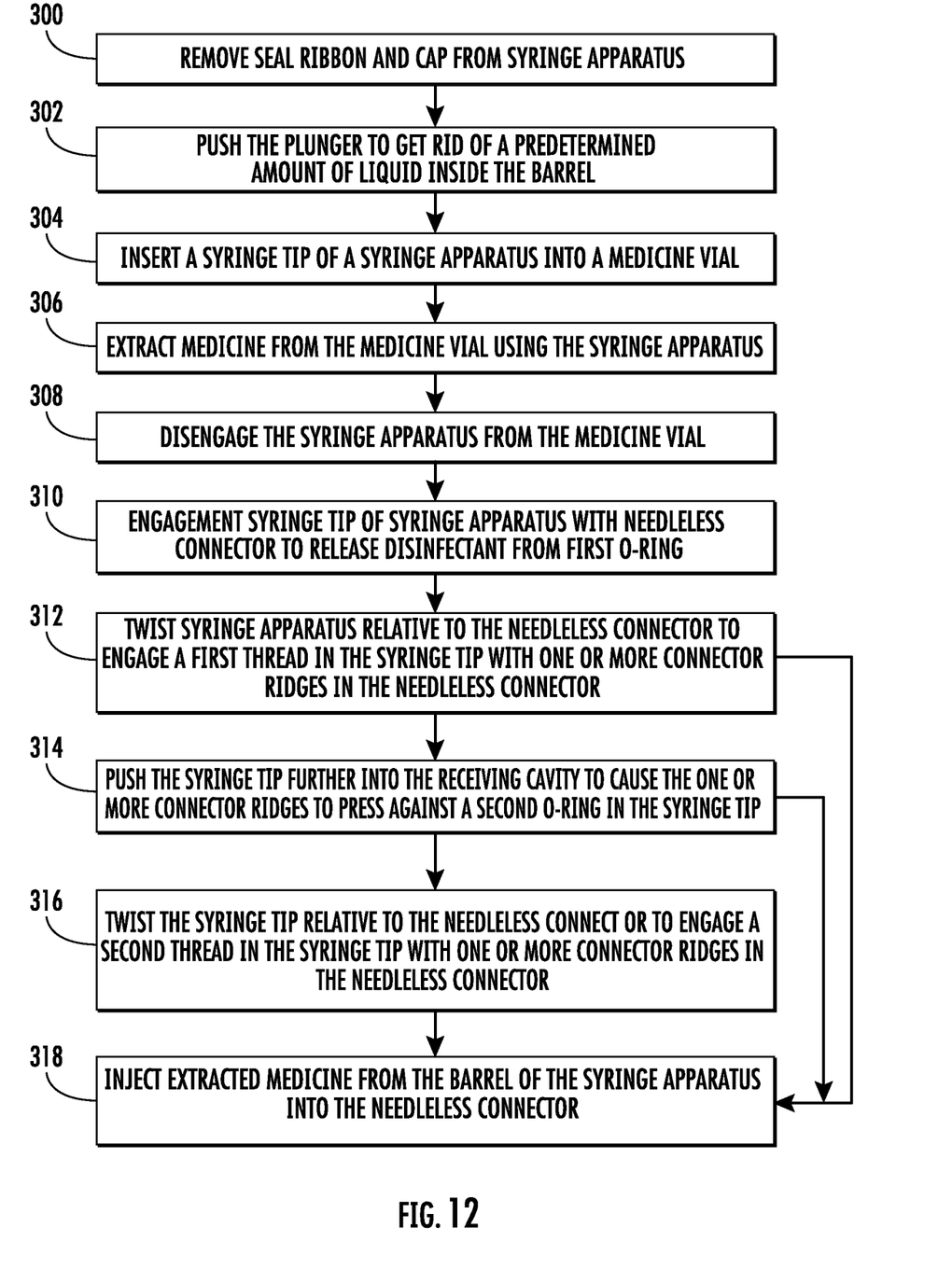
FIG. 12 shows a flow chart of method steps for using the syringe apparatus shown in FIGS. 1-9 for extracting medicine from a medicine container and injecting the medicine into a central IV through a needleless connector.

FIG. 10 shows the syringe apparatus 100 in proximity to an example of a medicine vial 168. The syringe apparatus 100 can be used to extract medicine from the medicine vial 168 and then inject such medicine into a central IV line through a needleless connector as shown in the FIG. 12. Traditional syringes require a separate blunt tip attachment in order to draw up medication in vials, but the syringe apparatus 100 described herein requires no additional blunt tip attachment because it already has an extended blunt tip (i.e., the distal end 112 of the inner tip portion 104). In a preferred embodiment, a first step 300 (not shown) is the removal of the seal ribbon 152 and the cap 142. Preferably, a next action (step 302) includes gently pushing the plunger 110 to get rid of a determined amount of liquid inside the barrel 108. Now with less volume of liquid in the barrel 108 and before engaging the syringe tip 102 into a needless connector, the syringe tip 102 including the blunt distal end 112 of the inner tip portion 104 can be used to penetrate a medicine vial (step 304), draw and/or otherwise extract medicine out of the vial and into the syringe barrel 108 (step 306), disengage the syringe apparatus 100 from the medicine vial (step 308), and then engage the syringe tip 102 with a needleless connector (step 310) as shown in FIGS. 3-8. The initial engagement is the first "push" step (step 310) (similar to step 202 in FIG. 11), preferably followed by a first twist step (step 312) (similar to step 204 in FIG. 11), preferably followed by a second push step (step 314) (similar to step 206 in FIG. 11), and then preferably followed by a second twist step (step 316) (similar to step 208 in FIG. 11). Then, the medicine that was extracted and stored on the barrel 108 of the syringe apparatus 100 is injected into a patient's bloodstream by injecting the medicine into the needleless connector in fluid communication with a central IV (step 318). The shape and length of the inner tip portion 104 is an enhancement and improvement over contemporary syringe apparatuses used for saline flushes. The length of the inner tip portion 104 preferably ranges from about 16 mm to about 18 mm from the barrel 108 of the syringe apparatus 100.

The previously described embodiments of the present disclosure have many advantages. The early exposure of the disinfectant from the external section 148 of the inner tip portion 104 acts as a "scrubber" on top of any biofilm on the needleless connector 156. The disinfectant from the first O-ring 124 provides a means of properly disinfecting the entire needleless connector 156. The structure of the syringe apparatus 100 provides the most important factors in preventing CLABSIs, namely, friction and drying. Use of the syringe apparatus 100 avoids the need to "scrub the hub" and clean needleless connectors while providing the same benefits from traditional needleless connector cleaning steps. This is all done in less time with fewer steps to consider. After the cap 142 is removed from the syringe apparatus 100, the four steps to remember are push, twist, push, and twist. After these basic and simple steps, the Normal Saline fluid in the barrel 108 can be injected into a central IV line. Thus, the cleaning mechanism is part of the Normal Saline flush procedure which already requires connecting a syringe to a needleless connector by engaging Luer locks.

The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

Any element in a claim that does not explicitly state "means for" performing a specified function, or "step for" performing a specific function, is not to be interpreted as a "means" or "step" clause as specified in 35 U.S.C. § 112, ¶6. In particular, the use of "step of" in the claims herein is not intended to invoke the provisions of 35 U.S.C. § 112, ¶6.

What is claimed is:
1. A syringe apparatus comprising:
 a. a barrel;
 b. a plunger; and
 c. a syringe tip, the syringe tip further comprising:
  i. an inner tip portion extending from a first end of the barrel to a distal end of the syringe tip;
  ii. an outer tip portion concentrically positioned outside the inner tip portion, wherein the outer tip portion extends from a first end of the barrel to a distal end of the outer tip portion, and wherein the inner tip portion extends farther away from the barrel than the outer tip portion;
  iii. a tip cavity formed between the inner tip portion and the outer tip portion, the tip cavity comprising a first section proximate to the distal end of the outer tip portion, a second section adjacent to the first section located closer to the barrel than the first section, and a third section adjacent to the second section and located closer to the barrel than the second section;
  iv. a first sponge-like O-ring inside the first section wherein the O-ring comprises a first disinfectant substance absorbed into the O-ring;
  v. a first thread inside the second section extending inwardly and winding helically from an inner wall of the outer tip portion; and
  vi. a second sponge-like O-ring inside the third section wherein the second O-ring is dry.

2. The syringe apparatus of claim 1 wherein the outer tip portion flares outward along the distal end of the outer tip portion.

3. The syringe apparatus of claim 1 wherein the syringe tip further comprises: ii. the tip cavity further comprising a fourth section adjacent to the third section and located closer to the barrel than the third section; and iii. a second thread inside the fourth section extending inwardly and winding helically from the inner wall of the outer tip portion.

4. The syringe apparatus of claim 1 further comprising a cap attached to the outer tip portion, the cap further comprising:
 ii. an outer shell; and
 iii. an inner layer comprising a second disinfectant substance absorbed into the inner layer.

5. The syringe of claim 4 further comprising a seal ribbon wrapped around the interface between the cap and the outer tip portion, providing an air-tight seal that prevents drying of the first disinfectant substance in the cap and the second disinfectant substance in the first O-ring.

6. The syringe apparatus of claim 5 wherein the first disinfectant substance comprises the second disinfectant substance.

7. The syringe apparatus of claim 5 wherein the outer tip portion further comprises an outer ridge along the distal end of the outer tip portion, wherein the cap further comprises a bulge along a base of the cap, and wherein the seal ribbon is wrapped around the outer ridge and the bulge, sealing the cap to the outer tip portion.

8. The syringe apparatus of claim 4 further comprising a fluid in the barrel of the syringe apparatus wherein the fluid comprises a saline solution.

9. The syringe apparatus of claim 1 wherein the syringe tip further comprises:
  ii. the tip cavity further comprising a third section adjacent to the second section and located closer to the barrel than the second section; and
  iii. a second thread inside the third section extending inwardly and winding helically from the inner wall of the outer tip portion.

10. A method for disinfecting a needleless connector, the method comprising:
  a. inserting an inner tip portion of a syringe tip of a syringe apparatus into a receiving cavity of a needleless connector until a first end of the needleless connector reaches an outer tip portion of the syringe tip and compresses a first sponge-like O-ring inside a tip cavity of the syringe tip defined between the inner tip portion and the outer tip portion to release disinfectant stored in the first O-ring onto the needleless connector;
  b. twisting the syringe apparatus relative to the needleless connector to engage a first thread in the syringe tip with one or more connector ridges in the needleless connector; and
  c. pushing the syringe tip further into the receiving cavity to cause the one or more connector ridges to press against a second sponge-like O-ring in the tip cavity of the syringe tip wherein the second sponge-like O-ring is initially dry.

11. The method of claim 10 further comprising twisting the syringe tip relative to the needleless connector to engage a second thread in the syringe tip with one or more connector ridges in the needleless connector.

12. A method for injecting medicine into a patient through a central IV line, the method comprising:
  a. displacing liquid from a barrel of a syringe apparatus by pushing a plunger of the syringe inward;
  b. inserting a syringe tip of the syringe apparatus into a medicine vial;
  c. extracting medicine from the medicine vial using the syringe apparatus;
  d. disengaging the syringe apparatus from the medicine vial;
  e. inserting an inner tip portion of a syringe tip of a syringe apparatus into a receiving cavity of a needleless connector in fluid communication with a patient's bloodstream until a first end of the needleless connector reaches an outer tip portion of the syringe tip and compresses a first sponge-like O-ring inside a tip cavity of the syringe tip defined between the inner tip portion and the outer tip portion to release disinfectant stored in the first sponge-like O-ring onto the needleless connector, wherein the inserting step further comprises twisting the syringe tip relative to the needleless connector to engage a first thread in the syringe tip with one or more connector ridges in the needleless connector and pushing the syringe tip further into the receiving cavity to cause the one or more connector ridges to press against a second sponge-like O-ring in the syringe tip; and
  f. injecting the extracted medicine from the syringe apparatus to the patient by injecting the extracted medicine to the needleless connector.

13. The method of claim 12 wherein the syringe tip used in the method comprises:
  ii. an inner tip portion extending from a first end of a barrel of the syringe apparatus to a distal end of the syringe tip;
  iii. an outer tip portion concentrically positioned outside the inner tip portion, wherein the outer tip portion extends from a first end of the barrel to a distal end of the outer tip portion a distance of length L, and wherein the inner tip portion extends away from the barrel than the outer tip portion a distance of greater than the length L.

14. The method of claim 12 wherein the distal end of the syringe tip comprises a multi-faceted blunt tip.

15. The method of claim 12 wherein the inserting step e further comprises twisting the syringe tip relative to the needleless connector to engage a second thread in the syringe tip with one or more connector ridges in the needleless connector.

* * * * *